United States Patent [19]

Bru-Magniez et al.

[11] Patent Number: 4,931,584

[45] Date of Patent: Jun. 5, 1990

[54] PROCESS FOR THE PREPARATION OF MONOESTERS OR DIESTERS OF 9,10-ENDOETHANO-9,10-DIHYDROAN-THRACENE-11,11-DICARBOXYLIC ACID NOVEL MONOESTERS OF DIESTERS PREPARED BY THIS PROCESS AND USE THEREOF FOR THE PREPARATION OF SYMMETRICAL OR ASYMMETRICAL METHYLIDENEMAL

[75] Inventors: Nicole Bru-Magniez, Paris, France; Christian De Cock, St Genese, Belgium; Jacques Poupaert, Ottignies-Louvain la Neuve, Belgium; Jean-Luc De Keyser, Tervuren, Belgium; Pierre Dumont, Gembloux, Belgium

[73] Assignee: Laboratoires UPSA, France

[21] Appl. No.: 162,573

[22] Filed: Mar. 1, 1988

[30] Foreign Application Priority Data

Mar. 5, 1987 [FR] France ............................... 87 02991

[51] Int. Cl.$^5$ ............................................. C07C 67/343
[52] U.S. Cl. ...................... 560/190; 549/513; 549/557; 549/265; 549/562; 558/365; 558/406; 560/80; 560/193; 560/197; 560/198; 560/201; 562/488
[58] Field of Search .............. 560/6, 80, 193, 197, 560/198, 201, 190; 562/403, 595, 488; 549/543, 265, 513, 557, 562; 558/365, 406

[56] References Cited

U.S. PATENT DOCUMENTS 2,212,506 8/1940 Bachman .................. 560/80

*Primary Examiner*—Michael L. Shippen
*Attorney, Agent, or Firm*—Marshall & Melhorn

[57] ABSTRACT

The invention relates to novel monoesters and diesters of 9,10-endoethano-9,10-dihydroanthracene-11,11-dicarboxylic acid.

These novel monoesters and diesters correspond to the following structural chemical formula (II):

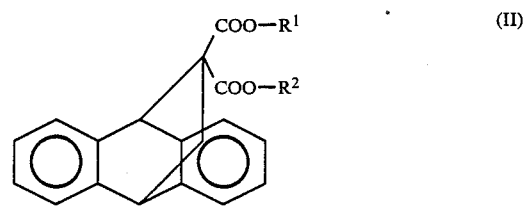

in which $R^1$ and $R^2$ are identical or different and can represent H, an alkali metal or alkaline earth metal atom, a linear or branched alkyl group having from 1 to 6 carbon atoms, an alicyclic group having from 3 to 6 carbon atoms, an alkenyl group having from 2 to 6 carbon atoms, defined in their cis or trans variety, or an alkynyl group having from 2 to 6 carbon atoms, the said groups optionally being substituted by one or more functional groups such as ether, epoxide, halogeno, cyano, ester, aldehyde, ketone, aryl etc., where $R^1$ and $R^2$ cannot be H or ethyl simultaneously. These addition products constitute valuable intermediates for the preparation of methylidenemalonates in high yields and with a high purity.

12 Claims, No Drawings

PROCESS FOR THE PREPARATION OF MONOESTERS OR DIESTERS OF-9,10-ENDOETHANO-9,10-DIHYDROANTHRACENE-11,11-DICARBOXYLIC ACID AND FOR THE PREPARATION OF SYMMETRICAL OR ASYMMETRICAL METHYLIDENEMALONATES

The present invention relates to a process for the preparation of monoesters or diesters of 9,10-endoethano-9,10-dihydroanthracene-11,11-dicarboxylic acid, the novel monoesters or diesters prepared by this process and the use thereof for the preparation of symmetrical or asymmetrical methylidenemalonates.

More particularly, the monoester or diester derivatives according to the invention make it possible to prepare methylidenemalonates of the following formula (I):

$$CH_2=C(COOR^1)(COOR^2) \qquad (I)$$

in which $R^1$ and $R^2$ represent linear or branched alkyl groups of 1 to 6 carbon atoms, alicyclic groups having from 3 to 6 carbon atoms, alkenyl groups having from 2 to 6 carbon atoms, defined in their cis or trans variety, or alkynyl groups having from 2 to 6 carbon atoms, the said groups optionally being substituted by functional groups such as ether, epoxide, halogeno, cyano, ester, aldehyde or ketone, aryl etc.

The value of the compounds of formula (I) mentioned above is well known both in organic synthesis and in polymer chemistry.

Numerous processes have already been described which make it possible to prepare methylidenemalonates with a formula similar to formula (I) above.

For example, a basic process consists in reacting diethyl malonate with formaldehyde in glacial acetic acid, in the presence of catalysts based on a metal acetate, to produce diethyl methylidenemalonate by distillation, after the catalyst has been filtered off and the solvent has been separated off.

The methylidenemalonate can then be used for polymerization (Chemical Abstracts 1953, vol. 49, abstract 6836d). The same basic reaction is described in Chemical Abstracts, vol. 76, 1972, abstract 139905m. For the polymerization, see "Die Makromolekulare Chemie" 107 (1967), p. 4–5.

However, under the usual conditions of this thermal decomposition of the hydroxyl compound initially formed by the reaction of the malonate with formaldehyde, the above-mentioned methylidenemalonate (I) obtained polymerizes, except in the case where $R^1$ and $R^2$ are represented by the t-butyl group (see P. BALLESTEROS, B. W. ROBERTS and J. WANG, J. Org. Chem. 48, 3603–3605 (1983)).

Furthermore, it has already been proposed to prepare symmetrical or asymmetrical methylidenemalonates by reacting a malonic acid diester with formaldehyde, in the presence of a diene, to give a Diels-Alder addition product, which is then subjected to pyrolysis to give the methylidenemalonate.

Thus, in British Patent Document No. A-1 560 323 to EASTMAN KODAK, the diene used is a linear diene, such as a substituted pentadiene, a hexadiene, isoprene or unsubstituted or substituted buta-1,3-diene, and the intermediate addition product is then pyrolyzed at 600° C. to release the methylidenemalonate.

Moreover, German Patent Document No. C-27 34 082 to PONTICELLO also describes the preparation of asymmetrical methylidenemalonates by carrying out a reaction of the Diels-Alder type between a methyl acrylate and cyclopentadiene to give an intermediate addition product, which is then subjected to various chemical reactions to give a diester before decomposition by pyrolysis to yield the asymmetrical methylidenemalonate diester.

Again, the synthesis of an alkyl alpha-cyanoacrylate by reacting a cyanoacrylic acid ester with a conjugated diene, exemplified by anthracene, is also known; this forms the Diels-Alder addition product, which is then hydrolyzed (see U.S. Pat. Document No. A-3 975 422 or GIRAL, Annal. Pharmaceutiques Francaises 1985, 43, no. 5, pages 439–449, or U.S. Pat. Document No. 4 056 543 to PONTICELLO); here, however, the cyanoacrylic acid ester initially contains a unit of unsaturation which is used for the addition reaction with the anthracene. This type of addition reaction is very old and had already been described by BACHMAN and TANNER in J. Org. Chem. 4 (1939), p. 500. It has been used to purify previously formed methylidenemalonate by an addition reaction with cyclopentadiene or norbornene (see C.A., vol. 95, 1981, abstract 168570w).

Thus, as far as those skilled in the art are concerned, the use of anthracene has only been described for the formation of an addition product with an unsaturated compound, namely previously formed diethyl methylidenemalonate or a cyanoacrylic acid ester.

Furthermore, the state of the art, in the form of British Patent Document No. A-1 560 323 mentioned above, teaches those skilled in the art how to use a linear diene to trap the methylidenemalonate in situ during the reaction of a malonate with formaldehyde. Thus, from the point of view of those skilled in the art, this type of trapping process in situ using a cyclic diene did not appear possible, undoubtedly because of the unfavorable reaction conditions.

Now, it has just been discovered, totally unexpectedly and in contradiction to the teaching of the state of the art, that anthracene is a conjugated diene which does make it possible for the methylidenemalonate formed in situ by the reaction of malonate with formaldehyde to be trapped very efficiently (i.e. with excellent yields) and very simply, in situ, the addition product formed being readily crystallizable.

To summarize, all the present methods of synthesis have major disadvantages which make them difficult, if not impossible, to adapt to the industrial scale.

Thus, the direct formation of methylidenemalonate cannot be used because it leads to inevitable polymerization of the methylidenemalonate formed.

In cases where an intermediate addition product is prepared, this is often difficult to filter off and purify by recrystallization and is always contaminated by considerable quantities of conjugated dienes used for the Diels-Alder reaction, this contamination affecting the subsequent, thermolysis or hydrolysis step. In the processes of the prior art, purification by distillation under a high vacuum is therefore necessary in this case.

In addition, the yields are generally relatively modest and the number of steps required to form methylidenemalonate is relatively large, especially in the case where asymmetrical esters are formed.

The object of the present invention is therefore to solve the new technical problem of providing a new process for the synthesis of methylidenemalonate which can be used on the industrial scale, is very simple and reliable, uses inexpensive reactants, has a minimum number of steps, preferably only two main steps, gives products of high purity in high yields and makes it possible to prepare a wide range of products, including those carrying reactive groups on the above-mentioned ester substituents $R^1$ and $R^2$.

Another main object of the present invention is to solve the new technical problem of forming asymmetrical methylidenemalonates and in particular those in which one of the esters has been substituted by at least one functional group such as ether, epoxide, halogen, cyano, ester, aldehyde, ketone, aryl etc.

Another object of the present invention is to solve the new technical problem of providing a new process for the synthesis of methylidenemalonate by the formation of an addition product or adduct of the Diels-Alder type very simply and very rapidly, in a high yield, this addition compound advantageously being capable of undergoing hemihydrolysis—which was previously impossible—enabling asymmetrical addition products to be prepared, as desired, by alkylation with an appropriate halide.

Another object of the present invention is to solve the new technical problem of forming novel intermediate addition products which can be used for the synthesis of methylidenemalonate and are capable of being isolated easily by crystallization, with a high purity, whereby small amounts of contaminants in no way affect their ability to form methylidenemalonates in a subsequent step, these addition products being symmetrical or, advantageously, asymmetrical esters or monoesters.

Preferably, these addition products enable methylidenemalonate to be obtained by thermolysis at considerably lower temperatures than in the case of other known addition products.

Moreover, the invention also provides a solution which uses solvents of low toxicity to facilitate the extraction and isolation of the addition products.

All these new technical problems are solved for the first time by the present invention, very simply and rapidly, with the formation of addition products and methylidenemalonate with a high purity and in high yields.

Thus, according to a first aspect, the present invention provides a process for the preparation of monoesters or diesters of 9,10-endoethano-9,10-dihydroanthracene-11,11-dicarboxylic acid of the following formula (II):

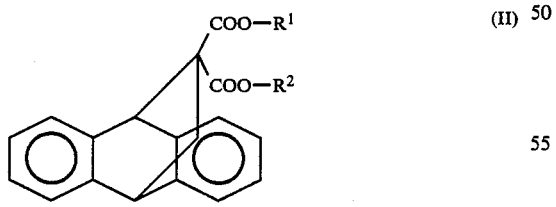

in which $R^1$ and $R^2$ can be identical or different and can represent H, an alkali metal or alkaline earth metal atom, especially sodium or potassium, a linear or branched alkyl group having from 1 to 6 carbon atoms, an alicyclic group having from 3 to 6 carbon atoms, an alkenyl group having from 2 to 6 carbon atoms, defined in their cis or trans variety, or an alkynyl group having from 2 to 6 carbon atoms, the said groups optionally being substituted by one or more functional groups such as ether, epoxide, halogeno, cyano, ester, aldehyde, ketone, aryl etc., where $R^1$ and $R^2$ cannot be H simultaneously, which comprises reacting a corresponding malonic acid ester with formaldehyde, in the presence of anthracene, so as to give the said monoester or diester in the form of an addition product, and preferably separating this monoester or diester from the reaction medium so that it can be obtained, advantageously, in the form of a crystalline product.

In an advantageous embodiment of this process, the reaction takes place in a non-aqueous solvent medium in the presence of a catalyst which is preferably selected from copper(II) acetate, potassium acetate and mixtures thereof.

Advantageously, this non-aqueous solvent is selected from a water-immiscible solvent and, advantageously, a water-miscible solvent. The following may be mentioned among these solvents: acetic acid, acetic anhydride, benzene, bromobenzene, xylene, toluene, dimethylformamide (DMF), dimethyl sulfoxide (DMSO), a ketone such as dimethyl ketone or ethyl methyl ketone, acetonitrile, dioxane, N-methylpyrrolidone (NMP) or any mixture of at least 2 or 3 of these solvents.

In an advantageous embodiment, the monoester addition products are synthesized from the diester derivatives, preferably by reaction, in an alcoholic solvent, with an alkali metal or alkaline earth metal salt and especially sodium or potassium hydroxide.

In an equally advantageous embodiment, the asymmetrical diester addition products are prepared from the monoester addition product by reaction with a halogen-containing product whose radical is to form a second ester radical which is different from the first ester radical.

In an advantageous modified embodiment of the process, the reaction is carried out in a closed system, in particular in an autoclave or Carius tube.

According to a second aspect, the present invention also provides novel monoesters and diesters of 9,10-endoethano-9,10-dihydroanthracene-11,11-dicarboxylic acid which advantageously correspond to the following structural chemical formula (II):

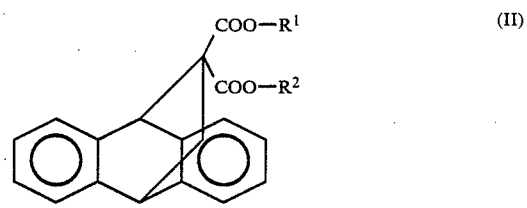

in which $R_1$ and $R_2$ can be identical or different and can represent H, an alkali metal or alkaline earth metal atom, especially sodium or potassium, a linear or branched alkyl group having from 1 to 6 carbon atoms, an alicyclic group having from 3 to 6 carbon atoms, an alkenyl group having from 2 to 6 carbon atoms, defined in their cis or trans variety, or an alkynyl group having from 2 to 6 carbon atoms, the said groups optionally being substituted by one or more functional groups such as ether, epoxide, halogeno, cyano, ester, aldehyde, ketone, aryl etc., whereby $R^1$ and $R^2$ cannot be H or an ethyl group simultaneously.

In particular, the invention includes the following monoesters and diesters, which constitute intermediate addition products for the preparation of methylidenemalonates:

11,11-di-n-propoxycarbonyl-9,10-endoethano-9,10-dihydroanthracene,
11,11-di-n-butoxycarbonyl-9,10-endoethano-9,10-dihydroanthracene,
11-n-butoxycarbonyl-11-n-pentoxycarbonyl-9,10-endoethano-9,10-dihydroanthracene,
11-ethoxycarbonyl-11-ethoxycarbonylmethoxycarbonyl-9,10-endoethano-9,10-dihydroanthracene,
11,11-dimethoxycarbonyl-9,10-endoethano-9,10-dihydroanthracene,
11-methoxycarbonyl-11-n-butoxycarbonyl-9,10-endoethano-9,10-dihydroanthracene,
11-methoxycarbonyl-11-n-hexyloxycarbonyl-9,10-endoethano-9,10-dihydroanthracene,
11-methoxycarbonyl-11-benzyloxycarbonyl-9,10-endoethano-9,10-dihydroanthracene,
11,11-diethoxycarbonyl-9,10-endoethano-9,10-dihydroanthracene,
11-ethoxycarbonyl-11-n-propoxycarbonyl-9,10-endoethano-9,10-dihydroanthracene,
11-ethoxycarbonyl-11-n-butoxycarbonyl-9,10-endoethano-9,10-dihydroanthracene,
11-ethoxycarbonyl-11-allyloxycarbonyl-9,10-endoethano-9,10-dihydroanthracene,
11-ethoxycarbonyl-11-prop-3-ynyloxycarbonyl-9,10-endoethano-9,10-dihydroanthracene,
11-ethoxycarbonyl-11-methoxymethoxycarbonyl-9,10-endoethano-9,10-dihydroanthracene,
11-ethoxycarbonyl-11-ethoxyethoxycarbonyl-9,10-endoethano-9,10-dihydroanthracene,
11-ethoxycarbonyl-11-ethoxycarbonylpropoxycarbonyl-9,10-endoethano-9,10-dihydroanthracene,
11-ethoxycarbonyl-11-(2′,3′-epoxypropoxycarbonyl)-9,10-endoethano-9,10-dihydroanthracene,
11-ethoxycarbonyl-11-propan-3-olyloxycarbonyl-9,10-endoethano-9,10-dihydroanthracene,
11-n-propoxycarbonyl-11-n-butoxycarbonyl-9,10-endoethano-9,10-dihydroanthracene,
11,11-diisopropoxycarbonyl-9,10-endoethano-9,10-dihydroanthracene,
11,11-diisobutoxycarbonyl-9,10-endoethano-9,10-dihydroanthracene,
11,11-di-n-pentoxycarbonyl-9,10-endoethano-9,10-dihydroanthracene,
11,11-diallyloxycarbonyl-9,10-endoethano-9,10-dihydroanthracene and
11,11-trimethylene-1′,3′-dioxycarbonyl-9,10-endoethano-9,10-dihydroanthracene.

Finally, according to a third aspect, the invention also includes the use of the monoesters or diesters for the preparation of methylidenemalonates by any treatment known per se, such as a heat treatment, thermolysis, pyrolysis or else hydrolysis.

Other objects, characteristics and advantages of the invention will become clearly apparent from the following explanatory description, which gives a few preparative examples simply by way of illustration and hence without in any way limiting the scope of the invention.

EXAMPLE 1

Preparation of 11,11-diisopropoxycarbonyl-9,10-endoethano-9,10-dihydroanthracene (II, $R^1 = R^2 =$ iso-$C_3H_7$)

188 g (1 mol) of diisopropyl malonate are heated to 90°–100° C. by means of an oil bath, with stirring, in the presence of 60 g (2 mol) of paraformaldehyde, 178 g (1 mol) of anthracene, 10 g of copper(II) acetate and 10 g of potassium acetate in 500 ml of acetic acid and 500 ml of bromobenzene. The temperature is maintained at 90°–100° C. for 2 hours. The temperature of the oil bath is then raised gradually so as to distil initially an azeotropic mixture composed of water, bromobenzene and acetic acid and then the residual acetic acid. Distillation is stopped when the copper(II) and potassium acetates precipitate. The reaction medium is cooled to 60° C. and the poured into 1 l of toluene. This mixture is cooled to 10° C. and filtered on a Büchner funnel and the filtrate is evaporated to dryness. The solid residue is recrystallized from ethanol. The product obtained in this way has a purity of 94%; it is contaminated (6%) with anthracene. The product purified by chromatography on a column of silica gel (hexane/isopropanol: 95/5 v/v) has a melting point of 136°–7° C.; yield: 72% (278.16 g). This compound analyzes correctly for the formula $C_{24}H_{26}O_4$.

EXAMPLE 2

Preparation of 11,11-diallyloxycarbonyl-9,10-endoethano-9,10-dihydroanthracene (II, $R^1 = R^2 = CH_2-CH=CH_2$)

The procedure is the same as in Example 1 but the following amounts of reactants are used: 46 g (0.25 mol) of diallyl malonate, 15 g (0.5 mol) of paraformaldehyde, 44.5 g (0.25 mol) of anthracene, 5 g of copper(II) acetate and 5 g of potassium acetate in 120 ml of bromobenzene and 120 ml of acetic acid. After recrystallization, the product has a melting point of 85°–86° C. and the yield is 45% (41.35 g). This compound analyzes correctly for the formula $C_{24}H_{22}O_4$.

The following derivatives were also prepared by this process:

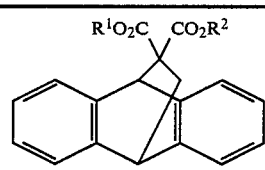

| $R^1$ | $R^2$ | Yield % | Melting point °C. | Elemental analysis |
|---|---|---|---|---|
| $CH_3$ | $CH_3$ | 53 | 161–162 | $C_{20}H_{18}O_4$ |
| $CH_3$ | n-$C_4H_9$ | 51 | 80–82 | — |
| $CH_3$ | n-$C_6H_{13}$ | 53 | 74–75 | — |
| $CH_3$ | $CH_2C_6H_5$ | 42 | 109–112 | — |
| $C_2H_5$ | $C_2H_5$ | 75 | 130–131 | $C_{22}H_{22}O_4$ |
| $C_2H_5$ | n-$C_3H_7$ | 82 | 107–108 | $C_{23}H_{24}O_4$ |
| $C_2H_5$ | n-$C_4H_9$ | 46 | 91–92 | — |
| $C_2H_5$ | $CH_2-CH=CH_2$ | 84 | 88–89 | $C_{22}H_{22}O_4$ |

-continued

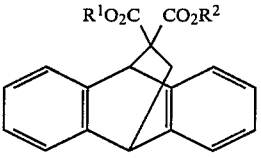

| $R^1$ | $R^2$ | Yield % | Melting point °C. | Elemental analysis |
|---|---|---|---|---|
| $C_2H_5$ | $CH_2-C\equiv CH$ | 62 | 60–61 | — |
| $C_2H_5$ | $CH_2OCH_3$ | 75 | 106–107 | $C_{22}H_{22}O_5$ |
| $C_2H_5$ | $C_2H_4OC_2H_5$ | 47 | 42–46 | — |
| $C_2H_5$ | $CH_2CO_2C_2H_5$ | 42 | 76–77 | — |
| $C_2H_5$ | $(CH_2)_3CO_2C_2H_5$ | 67 | 83–84 | — |
| $C_2H_5$ | $CH_2CH\overset{O}{\underset{}{\diagup\diagdown}}CH_2$ | 66 | 114–115 | $C_{23}H_{22}O_5$ |
| $C_2H_5$ | $CH_2CH_2CH_2-OH$ | 53 | 95–98 | — |
| $n-C_3H_7$ | $n-C_3H_7$ | 72 | 104–106 | $C_{24}H_{26}O_4$ |
| $n-C_3H_7$ | $n-C_4H_9$ | 47 | 91–92 | — |
| $iso-C_3H_7$ | $iso-C_3H_7$ | 72 | 136–137 | $C_{24}H_{26}O_4$ |
| $n-C_4H_9$ | $n-C_4H_9$ | 55 | 91–92 | $C_{26}H_{30}O_4$ |
| $iso-C_4H_9$ | $iso-C_4H_9$ | 52 | 94–95 | $C_{26}H_{30}O_4$ |
| $n-C_4H_9$ | $n-C_5H_{11}$ | 53 | 77–79 | — |
| $n-C_5H_{11}$ | $n-C_5H_{11}$ | 45 | 75–76 | — |
| $CH_2CH=CH_2$ | $CH_2CH=CH_2$ | 41 | 85–86 | — |
| $-CH_2-CH_2-CH_2-$ | | 53 | 115–118 | — |

EXAMPLE 3

Synthesis of the potassium salt of 11-ethoxycarbonyl-9,10-endoethano-9,10-dihydroanthracene-11-carboxylic acid (III, $R^1=C_2H_5$, $R^2=K$)

A solution of 18.6 g (0.324 mol) of potassium hydroxide in 400 ml of absolute ethanol is added dropwise, with stirring, to a solution of 100 g (0.286 mol) of 11,11-diethoxycarbonyl-9,10-endoethano-9,10-dihydroanthracene in 400 ml of absolute ethanol, heated to 65° C. After 4 hours, the reaction mixture is cooled to ordinary temperature and the potassium salt which has precipitated is filtered off and washed with diethyl ether. After drying in vacuo at ordinary temperature, 92 g (yield: 90%) of a white powder are obtained.

EXAMPLE 4

Synthesis of 11-allyloxycarbonyl-11-ethoxycarbonyl-9,10-endoethano-9,10-dihydroanthracene (II, $R^1=CH_2-CH=CH_2$, $R^2=C_2H_5$)

20 g (0.0555 mol) of (III) and 8.4 g (0.0555 mol) of allyl bromide are reacted in 250 ml of anhydrous dimethylformamide. The reaction medium is heated to 80° C., stirred for 2 hours, diluted in 2 l of water and filtered; the precipitate is washed with water and recrystallized from ethanol to give 17 g (85%) of a product with a melting point of 88°–89° C. This compound analyzes correctly for the formula $C_{23}H_{22}O_4$.

EXAMPLE 5

Synthesis of 11-(2',3'-epoxypropoxycarbonyl)-11-ethoxycarbonyl-9,10-endoethano-9,10-dihydroanthracene (II, $R^1=CH_2-\overline{CH-CH_2-O}$, $R^2=C_2H_5$)

The procedure is the same as in Example 4 but the following amounts of reactants are used: 20 g (0.0555 mol) of (III) and 8.9 g (0.065 mol) of epibromohydrin. The product is obtained with a yield of 70% after recrystallization from ethanol (melting point: 114°–115° C.). This compound analyzes correctly for the formula $C_{23}H_{22}O_5$.

EXAMPLE 6

Synthesis of 11,11-trimethylene-1',3'-dioxycarbonyl-9,10-endoethano-9,10-dihydroanthracene (II, $R^1R^2=-CH_2-CH_2-CH_2-$)

5 g (0.013 mol) of 11-ethoxycarbonyl-11-propan-3-olyloxycarbonyl-9,10-endoethano-9,10-dihydroanthracene (II, $R^1=C_2H_5$, $R^2=-C_2H_4-CH_2OH$), obtained by alkylation of the potassium salt (III, $R^1=C_2H_5$, $R^2=K$) with 3-bromopropan-1-ol in DMF, are reacted in 50 ml of xylene (dry) with a catalytic amount of NaH (60% dispersion in paraffin oil). A Vigreux column is fitted to the top of the round-bottomed flask and the mixture is heated so as to distil the xylene/ethanol azeotrope. After evaporation of the solvent, the solid residue is recrystallized from ethanol. Yield: 53% (2.52 g); melting point: 115°–118° C.

Examples 7 to 10 below relate to advantageous modified embodiments of the basic process for the preparation of the addition product (II).

EXAMPLE 7

Use of xylene in place of bromobenzene

This reduces the cost and the toxicity.

| Amount of solvent: | 1.5 volumes of xylene |
|---|---|
| | 1 volume of acetic acid |

The other conditions are identical to those described for bromobenzene in Example 1 but di-n-butyl malonate is used as the starting material in place of diisopropyl malonate.

11,11-Di-n-butoxycarbonyl-9,10-endoethano-9,10-dihydroanthracene (II, $R^1=R^2=$n—$C_4H_9$) is obtained; yield: 55%; melting point: 91°–92° C.

EXAMPLE 8

Use of a water-miscible solvent

The method of isolation is easier.

A range of solvents which ensured thermal conditions similar to the xylene (or bromobenzene) process but were water-miscible was studied. The distillation of high-boiling solvents is thus avoided, the reaction product being isolated by filtration after the addition of water.

The reaction mixture is cooled after being heated for 3 hours at 140° C. This mixture is poured into water and the solid is filtered off. The remainder of the process is identical to that of Example 1.

The yields given in the table are those obtained for the synthesis of 11,11-diethoxycarbonyl-9,10-endoethano-9,10-dihydroanthracene (II, $R^1=R^2=C_2H_5$) from diethyl malonate.

| Solvents (proportions v/v) | Yield % |
|---|---|
| DMF/acetic acid/$C_6H_6$ <br> 9    9    2 | 24 |
| DMSO/acetic acid <br> 1    1 | 8 |
| DMSO/acetic acid/dioxane <br> 2    0.8    2 | 25 |
| DMSO/acetic acid/toluene <br> 2    1    2 | 28 |
| NMP/acetic acid/xylene <br> 2    2    0.8 | 51 |

EXAMPLE 9

Use of an autoclave or a Carius tube Closed-system process

Example: synthesis of 11,11-diethoxycarbonyl-9,10-endoethano-9,10-dihydroanthracene An autoclave (capacity: 100 ml) is charged with 17 g of anthracene, 6 g of paraformaldehyde and 16 g of diethyl malonate.

The catalyst is a mixture of 0.5 g of cupric acetate and 0.5 g of potassium acetate.

The solvent (50 ml) is a mixture of acetic acid and benzene in the ratio 2.5/7.5 (v/v).

The autoclave is closed and then immersed for 2 hours in an oil bath heated to 90°–100° C. The temperature of the bath is raised gradually to 140°–150° C. over a period of 3 hours. The autoclave is cooled to room temperature and then opened. The reaction mixture is taken up with 100 ml of benzene. $CaCl_2$ (anhydrous) is added to the solution. After filtration, the solvents are evaporated off and the solid residue is recrystallized from ethanol. Yield: 67%; melting point: 127°–129° C.

The following table shows the different conditions examined. The amounts of reactants are identical to those described in the above example (unless indicated otherwise).

| Solvents (proportions v/v) | Catalyst | Yield |
|---|---|---|
| xylene/acetic acid <br> 1    1 | (Ac)$_2$Cu + AcK | 62% |
| benzene/acetic acid <br> 1    1 | (Ac)$_2$Cu + AcK | 41% |
| benzene/acetic acid <br> 7/8    1/8 | (Ac)$_2$Cu + AcK | 49% |
| benzene/acetic acid <br> 15/16    1/16 | (Ac)$_2$Cu + AcK | 46% |
| benzene/acetic acid <br> 3/4    1/4 | (Ac)$_2$Cu + AcK | 67% |
| benzene/acetic acid <br> 3/4    1/4 <br> (heating for 12 h) | (Ac)$_2$Cu + AcK | 46% |
| xylene/acetic acid/acetic anhydride <br> 2    2    1 | (Ac)$_2$Cu + AcK | 32% |
| xylene/acetic anhydride <br> 2    1 | (Ac)$_2$Cu + AcK | 32% |
| dimethyl ketone/acetic acid <br> 3/4    1/4 | (Ac)$_2$Cu + AcK | 56% |
| ethyl methyl ketone/acetic acid <br> 3/4    1/4 | (Ac)$_2$Cu + AcK | 63% |
| acetonitrile/acetic acid <br> 3/4    1/4 | (Ac)$_2$Cu + AcK | 58% |
| dioxane/acetic acid <br> 3/4    1/4 | (Ac)$_2$Cu + AcK | 56% |
| dioxane/acetic acid <br> 3/4    1/4 | (ClCH$_2$CO$_2$)$_2$Mg <br> 1 g | 31% |
| dimethyl ketone/acetic acid <br> 3/4    1/4 | (ClCH$_2$CO$_2$)$_2$Mg <br> 1 g | 26% |
| xylene/acetic acid/acetic anhydride <br> 5    5    2 | (ClCH$_2$CO$_2$)$_2$Mg <br> 1 g | 56% |
| benzene/acetic acid <br> 3/4    1/4 | (ClCH$_2$CO$_2$)$_2$Mg <br> 1 g + (Ac)$_2$Cu 0.5 g + AcK 0.5 g | 60% |
| methyl ethyl ketone/acetic acid <br> 3/4    1/4 | (Ac)$_2$Cu <br> 2.5 g | 75% |

EXAMPLE 10

Synthesis of 1,1-diisopropoxycarbonylethene (I, $R^1=R^2=$iso-$C_3H_7$)

50 g (0.132 mol) of the adduct described in Example 1 and 10.37 g (0.105 mol) of maleic anhydride are dispersed in 250 ml of mineral oil, with thorough stirring and under a stream of dry nitrogen. This suspension is heated gradually to 200°–220° C. This temperature is maintained for 45 minutes, after which the reaction mixture is cooled to ordinary temperature, placed under a vacuum (0.1 Torr) and distilled. The fraction boiling at 40° C. is collected. Yield: 64% (16.89 g). Purity: 99% (contaminant: 1% of maleic anhydride). Mass spectrum (70 eV), chemical ionization (isobutane): 201 (M+1), 159, 117.

EXAMPLE 11

Synthesis of 1-allyloxycarbonyl-1-ethoxycarbonylethene (I, $R^1=C_2H_5$, $R^2=CH_2$—CH=$CH_2$)

The procedure is the same as that described in Example 10 but the reactants used are 10 g (0.0276 mol) of the adduct of Example 4 and 2.16 g (0.022 mol) of maleic anhydride in 70 ml of mineral oil. The product obtained after distillation under 0.25 Torr has a boiling point of 53° C., the yield is 48% (2.4 g) and the purity is 99% (contaminant: 1% of maleic anhydride).

Examples 10 and 11 are representative of the general method for the thermolysis of the adducts (II) in the presence of maleic anhydride.

The following are examples of compounds which can be prepared by this method:

$$H_2C=\begin{matrix}CO_2R^1\\CO_2R^2\end{matrix}$$

| $R^1$ | $R^2$ | Yield % | Boiling point °C. (Torr) |
|---|---|---|---|
| $CH_3$ | $CH_3$ | 54 | 80–82 (6) |
| $CH_3$ | $n-C_4H_9$ | 75 | 65–68 (0.4) |
| $CH_3$ | $n-C_6H_{13}$ | 77 | 80–85 (0.1) |
| $C_2H_5$ | $C_2H_5$ | 67 | 60–61 (0.25) |
| $C_2H_5$ | $C_3H_7$ | 63 | 52–55 (0.3) |
| $C_2H_5$ | $C_4H_9$ | 71 | 62–63 (0.2) |
| $C_2H_5$ | $CH_2-CH=CH_2$ | 48 | 53–55 (0.25) |
| $C_2H_5$ | $CH_2-C\equiv CH$ | 20 | 65–77 (0.3) |
| $C_2H_5$ | $C_2H_4OC_2H_5$ | 43 | 82–84 (0.2) |
| $C_2H_5$ | $CH_2CO_2C_2H_5$ | 62 | 98–99 (0.1) |
| $C_2H_5$ | $CH_2CH_2CH_2CO_2C_2H_5$ | 32 | 86–89 (0.06) |
| $n-C_3H_7$ | $n-C_3H_7$ | 81 | 77–78 (0.2) |
| $n-C_3H_7$ | $n-C_4H_9$ | 54 | 78–80 (0.1) |
| $iso-C_3H_7$ | $iso-C_3H_7$ | 64 | 40–42 (0.1) |
| $n-C_4H_9$ | $n-C_4H_9$ | 68 | 76–80 (0.01) |
| $n-C_4H_9$ | $n-C_5H_{11}$ | 78 | 95–96 (0.1) |
| $n-C_5H_{11}$ | $n-C_5H_{11}$ | 46 | 99–101 (0.05) |
| isobutyl | isobutyl | 61 | 64–65 (0.02) |
| allyl | allyl | 48 | 67–68 (0.3) |

Thus it is seen that the present invention makes it possible to prepare addition products with anthracene very simply and very rapidly, with a high purity and also in high yields. Moreover, it is possible to prepare asymmetrical addition products as the basic addition products can undergo hemihydrolysis in a basic medium to give an alkali metal or alkaline earth metal monosalt of an 11-alkoxycarbonyl-9,10-endoethano-9,10-dihydroanthracene-11-carboxylic acid, which, on alkylation with an appropriate halide $R^3$-X in dimethylformamide, yields the asymmetrical addition product in accordance with the attached scheme 2.

Thus, the asymmetrical addition product, treated at about 220° C. in a mineral oil, in the presence of maleic anhydride, or by any other means of thermolysis or pyrolysis, yields the corresponding olefin, i.e. the corresponding methylidenemalonate.

The process according to the invention thus makes it possible to prepare methylidenemalonates from malonate esters in two essential steps, namely, in a first step, the reaction of the malonic acid ester with formaldehyde in the presence of anthracene, in accordance with scheme 1 below, and, in a second step, the heat treatment of the addition product obtained in the first step to form the corresponding methylidenemalonate, this advantageously taking place in the presence of maleic anhydride so as to separate out the anthracene in the form of another addition product (scheme 1).

The present invention therefore includes all the means which constitute technical equivalents of the means described and claimed in the claims.

SCHEME: 1

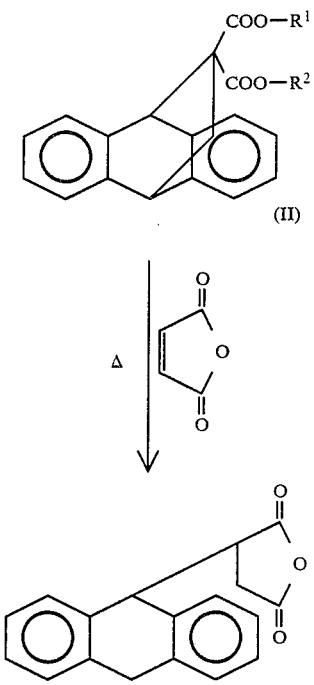

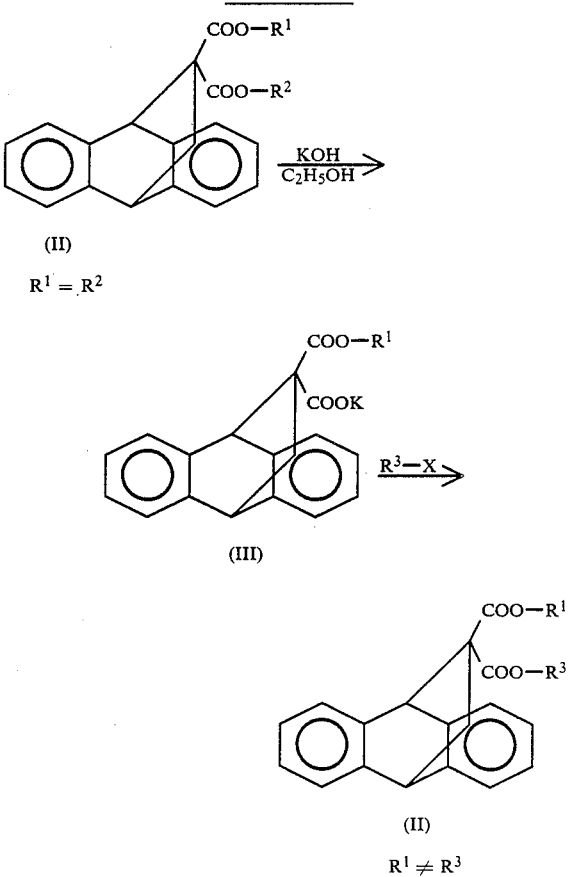

What is claimed is:

1. A process for the preparation of a monoester or diester of 9,10-endoethano-9,10-dihydroanthracene-11,11-dicarboxylic acid, comprising:
  contacting a malonic acid ester;
  with formaldehyde or paraformaldehyde;
  and with anthracene;
  in the presence of an effective amount of a catalyst, at an elevated temperature and for a time, sufficient to prepare a monoester or diester of 9,10-endoethano-9,10-dihydroanthracene-11,11-dicarboxylic acid corresponding to the general formula:

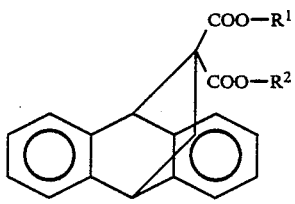

wherein $R^1$ and $R^2$ each, independently is hydrogen, a linear or branched alkyl radical having from 1 to 6 carbon atoms, an alkenyl radical having from 2 to 6 carbon atoms, or an alkynyl radical having from 2 to 6 carbon atoms, or $R^1$ and $R^2$ together form an alicyclic radical having from 3 to 6 carbon atoms, the alkyl, alicyclic, alkenyl, and alkynyl radicals optionally substituted with one or more ether, epoxy, halo, cyano, ester, aldehyde, keto, aryl, or hydroxy functional groups, with the proviso that $R^1$ and $R^2$ cannot both be hydrogen.

2. The process for the preparation of a monoester or diester, according to claim 1, wherein the catalyst is copper (II) acetate, potassium acetate, or a mixture thereof.

3. The process for the preparation of a monoester or diester, according to claim 1, wherein the contacting is carried out in the presence of a non-aqueous solvent.

4. The process for the preparation of a monoester or diester, according to claim 3, wherein the non-aqueous solvent is selected from the group consisting of acetic acid, acetic anhydride, benzene, bromobenzene, xylene, toluene, dimethylformamide, dimethyl sulfoxide, a ketone, acetonitrile, dioxane, N-methyl-pyrrolidone, and mixtures thereof.

5. A process for the preparation of a monoester salt of a diester of 9,10-endoethano-9,10-dihydroanthracene-11,11-dicarboxylic acid, comprising the steps of:
  (A) contacting a malonic acid ester;
  with formaldehyde or paraformaldehyde;
  and with anthracene;
  in the presence of an effective amount of a catalyst, at an elevated temperature and for a time, sufficient to prepare a diester of 9,10-endoethano-9,10-dihydroanthracene-11,11-dicarboxylic acid corresponding to the general formula:

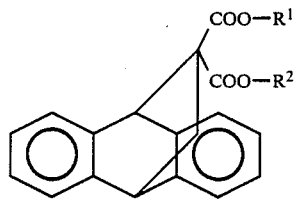

wherein $R^1$ and $R^2$ each, independently is a linear or branched alkyl radical having from 1 to 6 carbon atoms, an alkenyl radical having from 2 to 6 carbon atoms, or an alkynyl raidcal having from 2 to 6 carbon atoms, or $R^1$ and $R^2$ together form an alicyclic radical having from 3 to 6 carbon atoms, the alkyl, alicyclic, alkenyl, and alkynyl radicals optionally substituted with one or more ether, epoxy, halo, cyano, ester, aldehyde, keto, aryl, or hydroxy functional groups; and (B) contacting the diester with an alkali metal or alkaline-earth metal salt, in the presence of an alcohol;
so as to prepare a salt of a diester of 9,10-endoethano-9-10-dihydroanthracene-11,11-dicarboxylic acid corresponding to the general formula:

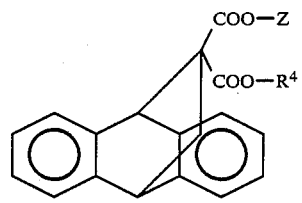

wherein Z is an alkali metal or alkaline-earth metal atom, and $R^4$ is a linear or branched alkyl radical having from 1 to 6 carbon atoms, an alkenyl radical having from 2 to 6 carbon atoms, or an alkynyl radical having from 2 to 6 carbon atoms, the alkyl, alkenyl, and alkynyl radicals optionally substituted with one or more ether, epoxy, halo, cyano, ester, aldehyde, keto, aryl, or hydroxy functional groups.

6. The process for the preparation of a monester salt, according to claim 5, wherein the alkali metal salt is sodium hydroxide or potassium hydroxide.

7. The process for the preparation of a monester salt, according to claim 5, wherein the alcohol is ethanol.

8. A process for the preparation of an asymmetrical diester of 9,10-endoethano-9,10-dihydroanthracene-11,11-dicarboxylic acid, comprising the steps of:
  (A) contacting a malonic acid ester;
  with formaldehyde or paraformaldehyde;
  and with anthracene;
  in the presence of an effective amount of a catalyst, at an elevated temperature and for a time, sufficient to prepare a diester of 9,10-endoethano-9,10-dihydroanthracene-11,11-dicarboxylic acid corresponding to the general formula:

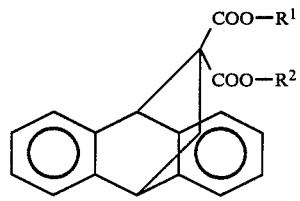

wherein $R^1$ and $R^2$ each, independently is a linear or branched alkyl radical having from 1 to 6 carbon atoms, an alkenyl radical having from 2 to 6 carbon atoms, or an alkynyl radical having from 2 to 6 carbon atoms, or $R^1$ and $R^2$ together form an alicyclic radical having from 3 to 6 carbon atoms, the alkyl, alicyclic, alkenyl, and alkynyl radicals optionally substituted with one or more ether, epoxy, halo, cyano, ester, aldehyde, keto, aryl, or hydroxy functional groups;

(B) contacting the diester with an alkali metal or alkaline-earth metal salt, in the presence of an alcohol;

so as to prepare a salt of a diester of 9,10-endoethano-9,10-dihydroanthracene-11,11-dicarboxylic acid corresponding to the general formula:

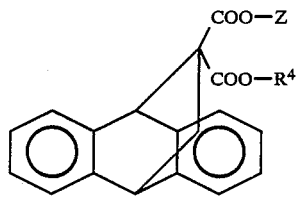

wherein Z is an alkali metal or alkaline-earth metal atom, and $R^4$ is a linear or branched alkyl radical having from 1 to 6 carbon atoms, an alkenyl radical having from 2 to 6 carbon atoms, or an alkynyl radical having from 2 to 6 carbon atoms, the alkyl, alkenyl, and alkynyl radicals optionally substituted with one or more ether, epoxy, halo, cyano, ester, aldehyde, keto, aryl, or hydroxy functional groups; and (C) contacting the monoester salt with a halogenated linear or branched alkane having from 1 to 6 carbon atoms, a halogenated alkene having from 2 to 6 carbon atoms, or a halogenated alkyne having from 2 to 6 carbon atoms, the halogenated alkane, alkene, and alkyne optionally substituted with one or more ether, epoxy, halo, cyano, ester, aldehyde, keto, aryl, or hydroxy functional groups;

so as to prepare an asymmetrical diester of 9,10-endoethano-9,10-dihydroanthracene-11,11-dicarboxylic acid corresponding to the general formula:

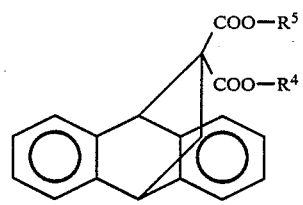

wherein $R^4$ and $R^5$ are different, and each, independently is a linear or branched alkyl radical having from 1 to 6 carbon atoms, an alkenyl radical having from 2 to 6 carbon atoms, or an alkynyl radical having from 2 to 6 carbon atoms, the alkyl, alkenyl, and alkynyl radicals optionally substituted with one or more ether, epoxy, halo, cyano, ester, aldehyde, keto, aryl, or hydroxy functional groups.

9. A process for the preparation of a methylidenemalonate, comprising the steps of:

(A) contacting a malonic acid ester;
with formaldehyde or paraformaldehyde;
and with anthracene;
in the presence of an effective amount of a catalyst, at an elevated temperature and for a time, sufficient to prepare a diester of 9,10-endoethano-9,10-dihydroanthracene-11,11-dicarboxylic acid corresponding to the general formula:

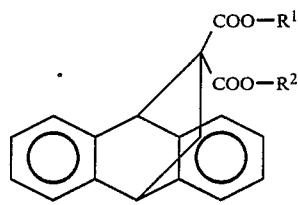

wherein $R^1$ and $R^2$ each, independently is a linear or branched alkyl radical having from 1 to 6 carbon atoms, an alkenyl radical having from 2 to 6 carbon atoms, or an alkynyl radical having from 2 to 6 carbon atoms, or $R^1$ and $R^2$ together form an alicyclic radical having from 3 to 6 carbon atoms, the alkyl, alicyclic, alkenyl, and alkynyl radicals optionally substituted with one or more ether, epoxy, halo, cyano, ester, aldehyde, keto, aryl, or hydroxy functional groups; and (B) contacting the diester with an alkali metal or alkaline-earth metal salt, in the presence of an alcohol;

so as to prepare a salt of a diester of 9,10-endoethano-9,10-dihydroanthracene-11,11-dicarboxylic acid corresponding to the general formula:

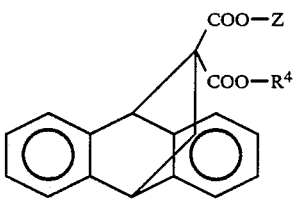

wherein Z is an alkali metal or alkaline-earth metal atom, and $R^4$ is a linear or branched alkyl radical having from 1 to 6 carbon atoms, an alkenyl radical having from 2 to 6 carbon atoms, or an alkynyl radical having from 2 to 6 carbon atoms, the alkyl, alkenyl, and alkynyl radicals optionally substituted with one or more ether, epoxy, halo, cyano, ester, aldehyde, keto, aryl, or hydroxy functional groups; and (C) thermally treating the diester;

so as to prepare a methylidenemalonate corresponding to the general formula:

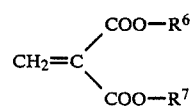

wherein $R^6$ and $R^7$ each, independently is a linear or branched alkyl radical having from 1 to 6 carbon atoms, an alkenyl radical having from 2 to 6 carbon atoms, or an alkynyl radical having from 2 to 6 carbon atoms, or $R^6$ and $R^7$ together form an alicyclic radical having from 3 to 6 carbon atoms, the alkyl, alicyclic, alkenyl, and alkynyl radicals optionally substituted with one or more ehter, epoxy, halo, cyano, ester, aldehyde, keto, aryl, or hydroxy functional groups.

10. The process for the preparation of a methylidenemalonate, according to claim 9, wherein the thermal treatment is carried out in the presence of maleic anhydride and a mineral oil.

11. A process for the preparation of a methylidenemalonate, comprising the steps of:
(A) contacting a malonic acid ester;
with formaldehyde or paraformaldehyde;
and with anthracene;
in the presence of an effective amount of a catalyst, at an elevated temperature and for a time, sufficient to prepare a diester of 9,10-endoethano-9,10-dihydroanthracene-11,11-dicarboxylic acid corresponding to the general formula:

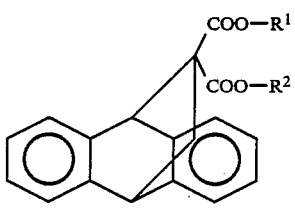

wherein $R^1$ and $R^2$ each, independently is a linear or branched alkyl radical having from 1 to 6 carbon atoms, an alkenyl radical having from 2 to 6 carbon atoms, or an alkynyl radical having from 2 to 6 carbon atoms, or $R^1$ and $R^2$ together form an alicyclic radical having from 3 to 6 carbon atoms, the alkyl, alicyclic, alkenyl, and alkynyl radicals optionally substituted with one or more ether, epoxy, halo, cyano, ester, aldehyde, keto, aryl, or hydroxy functional groups;

(B) contacting the diester with an alkali metal or alkaline-earth metal salt, in the presence of an alcohol;
so as to prepare a salt of a diester of 9,10-endoethano-9,10-dihydroanthracene-11,11-dicarboxylic acid corresponding to the general formula:

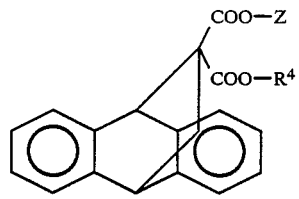

wherein Z is an alkali metal or alkaline-earth metal atom, and $R^4$ is a linear or branched alkyl radical having from 1 to 6 carbon atoms, an alkenyl radical having from 2 to 6 carbon atoms, or an alkynyl radical having from 2 to 6 carbon atoms, the alkyl, alkenyl, and alkynyl radicals optionally substituted with one or more ether, epoxy, halo, cyano, ester, aldehyde, keto, aryl, or hydroxy functional groups; and (C) contacting the monoester salt with a halogenated linear or branched alkane having from 1 to 6 carbon atoms, a halogenated alkene having from 2 to 6 carbon atoms, or a halogenated alkyne having from 2 to 6 carbon atoms, the halogenated alkane, alkene, and alkyne optionally substituted with one or more ether, epoxy, halo, cyano, ester, aldehyde, keto, aryl, or hydroxy functional groups;
so as to prepare an asymmetrical diester of 9,10-endoethano-9,10-dihydroanthracene-11,11-dicarboxylic acid corresponding to the general formula:

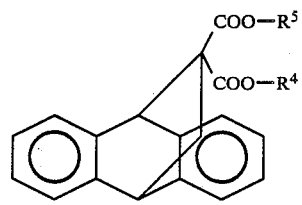

wherein $R^4$ and $R^5$ are different, and each, independently is a linear or branched alkyl radical having from 1 to 6 carbon atoms, an alkenyl radical having from 2 to 6 carbon atoms, or an alkynyl radical having from 2 to 6 carbon atoms, the alkyl, alkenyl, and alkynyl radicals optionally substituted with one or more ether, epoxy, halo, cyano, ester, aldehyde, keto, aryl, or hydroxy functional groups; and (D) thermally treating the diester;
so as to prepare a methylidenemalonate corresponding to the general formula:

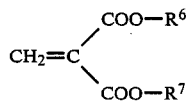

wherein $R^6$ and $R^7$ each, independently is a linear or branched alkyl radical having from 1 to 6 carbon atoms, an alkenyl radical having from 2 to 6 carbon atoms, or an alkynyl radical having from 2 to 6 carbon atoms, or $R_6$ and $R^7$ together form an alicyclic radical having from 3 to 6 carbon atoms, the alkyl, alicyclic, alkenyl, and alkynyl radicals optionally substituted with one or more ether, epoxy, halo, cyano, ester, aldehyde, keto, aryl, or hydorxy functional groups.

12. The process for the preparation of a methylidenemalonate, according to claim 11, wherein the thermal treatment is carried out in the presence of maleic anhydride and mineral oil.

* * * * *